United States Patent [19]

Tomita et al.

[11] Patent Number: 5,219,838
[45] Date of Patent: Jun. 15, 1993

[54] METHOD FOR INHIBITING TYROSINASE ACTIVITY IN TREATMENT OF SKIN

[75] Inventors: Mamoru Tomita; Seiichi Shimamura, both of Yokohama; Hiroshi Miyakawa, Kamakura; Susumu Kobayashi, Yokohama, all of Japan

[73] Assignee: Morinaga Milk Industry Co., Ltd., Tokyo, Japan

[21] Appl. No.: 884,051

[22] Filed: May 15, 1992

Related U.S. Application Data

[63] Continuation of Ser. No. 723,189, Jun. 28, 1991, abandoned.

[30] Foreign Application Priority Data

Jul. 9, 1990 [JP] Japan .................. 2-182343

[51] Int. Cl.$^5$ ............................................. A61K 37/48
[52] U.S. Cl. ........................................ 514/21; 514/8; 530/360; 530/365; 435/183
[58] Field of Search ............... 514/21, 8; 530/360, 530/365; 435/183

[56] References Cited

U.S. PATENT DOCUMENTS

| | | | |
|---|---|---|---|
| 3,061,512 | 10/1962 | Anderson Jr. et al. | 514/21 |
| 4,042,576 | 8/1977 | Eustache | 530/833 |
| 4,485,040 | 11/1984 | Roger et al. | 530/833 |
| 4,906,616 | 3/1990 | Gilchrist et al. | 530/832 |

FOREIGN PATENT DOCUMENTS

| | | | |
|---|---|---|---|
| 60-25810 | 2/1985 | Japan . | |
| 027641 | 8/1987 | Japan . | |
| 162971 | 11/1973 | United Kingdom | 530/360 |
| 2046591 | 11/1980 | United Kingdom . | |
| 2051076 | 1/1981 | United Kingdom . | |

*Primary Examiner*—Michael G. Wityshyn
*Assistant Examiner*—C. Sayala
*Attorney, Agent, or Firm*—Oblon, Spivak, McClelland, Maier & Neustadt

[57] ABSTRACT

An agent for tyrosinase inhibition which contains the effective quantity of enzymatic hydrolyzates of milk proteins, having a decomposition rate from 6% to 55% as expressed by the percentage of formol nitrogen to total nitrogen.

3 Claims, No Drawings

METHOD FOR INHIBITING TYROSINASE ACTIVITY IN TREATMENT OF SKIN

This application is a continuation of application Ser. No. 07/723,189, filed on Jun. 28, 1991, now abandoned.

BACKGROUND OF THE INVENTION

1. Field of the Invention

The present invention relates to a new use of enzymatic hydrolyzates of milk proteins. More particularly, the present invention relates to an agent for tyrosinase inhibition containing enzymatic hydrolyzates of milk proteins as an effective material for tyrosinase inhibition.

2. Discussion of the Background

Tyrosinase is known as an enzyme which may act as a catalyst for oxidization of tyrosin, other monohydric phenols or corresponding dihydric orthophenols with molecular oxygen and which widely occurs in plants such as mushrooms, potatoes, apples as well as in animal tissues. It is also known that tyrosinase is related to darkening phenomena at an injured portion of plant tissue, and is also related to formation of melanin pigment in various tissues of animals, especially in epidermal cells (Editorial Committee of Encyclopedia Chimica, Encyclopedia Chimica, Vol. 5, page 976, Kyohritsu Shuppan; 1960).

It is also known that pigmentation of melanin in epidermal cells or mucous membranes in Addison's disease is resulting from decrease in secretion of adrenal cortex hormones which antagonize melanotropin which in turn promotes tyrosinase activity (Editorial Committee of Encyclopedia Chimica, Encyclopedia Chimica, Vol. 1, page 65, Kyohritsu Shuppan; 1960).

Furthermore, it is said that tyrosinase is also related to degradation in freshness of foods.

Therefore, it has been strongly desired, in the industrial fields of pharmaceuticals, cosmetics, food and the like, to develop agents for tyrosinase inhibition and for prevention and therapy of symptoms resulting from undesirable effects of the activity of tyrosinase. Especially in the fields of cosmetic industry, earnest research has been actively made on cosmetics or medicines for external use for effective inhibition of tyrosinase, and many products containing agents for tyrosinase inhibition have been successively developed. There are known many agents for tyrosinase inhibition, for example, cystein, glutathione and vitamin C (Yutaka Mishima et al., Fundamental Dermatology, page 258, Asakura Shoten; 1973), Kojic acid (Nikkei Sangyo News Paper, May 24, 1988), arbutin (Kenichi Tomita, Preliminary Text for 20th F. J. Seminar, page 21, Fragrance Journal Company, Mar. 14, 1990), products of microorganisms belonging to the genus of Trichoderma (Unexamined Japanese Patent Application Gazette No. 2(1990)-145189).

In Examined Japanese Patent Application Gazette No. 58(1983)-17763, utilization of alkaline hydrolyzates of silk proteins in cosmetics as an agent for tyrosinase inhibition.

Conventional agents for tyrosinase inhibition, however, had more or less defects that they are unstable in the products, they have excessively potent function to melanocytes which produce melanin pigment, and they are too expensive due to the difficulty to obtain their raw materials, and they were not usable as cosmetics or medicines for external use from the view points of safety, preservability, reliability, economics and so on.

On the other hand, milk proteins and hydrolyzates thereof have been utilized in cosmetic products for various purposes such as moisturizing, film-forming (Unexamined Japanese Patent Application Gazette No 60(1985)-258102, Unexamined Japanese Patent Application Gazette No. 62(1987)-185100, Unexamined Japanese Patent Application Gazette No. 1(1989)-269499), and in the products of pharmaceutical and food industries for the purposes of increase in digestibility and absorbability, improvement in nutritional efficiency, and prevention from or treatment of allergy.

Recently, it has been reported that peptides included in milk protein hydrolyzates have physiological properties, for example, calcium absorption promoting property of $\beta$-casein phosphopeptide and proliferation promoting property of Bifidobacteria of $\kappa$-casein glycomacropeptide (Shokuhin Kogyo, Vol. 33, No. 1, page 31, 1990).

therefore, research has been actively made for the application of milk protein hydrolyzates in functional foods and drugs, however, it has not been known that peptides included in milk protein hydrolyzates have the activity of tyrosinase inhibition.

The inventors of the present invention have performed a research with respect to the agent for tyrosinase inhibition which has no defects in conventional agents for tyrosinase inhibition and which is usable for foods and drugs and which is stable and safe when it is used in such products, and found that enzymatic hydrolyzates of milk proteins surprisingly have activity of tyrosinase inhibition. The present invention is based on this discovery.

It should be noted that some of the inventors of the present invention and others have made inventions with respect to an agent for tyrosinase inhibition consisting of or containing lactoferrin or its hydrolyzates, and applications for patent have been filed in Japan by the same assignee of the present invention (Japanese Patent Application Nos. 2(1990)-169636 and 2(1990)-169637). Therefore, the objective substances of the present invention are the hydrolyzates of milk protein exclusive of lactoferrin, but when the present invention is actually carried out, it is not necessary to exclude lactoferrin from the milk protein as the raw material.

OBJECTS OF THE INVENTION

Therefore, it is an object of the present invention to provide hydrolyzates of milk proteins exclusive of lactoferrin usable as an agent for tyrosinase inhibition or an ingredient of preparations for tyrosinase inhibition.

It is another object of the present invention to provide an agent for tyrosinase inhibition consisting of or comprising hydrolyzates of milk proteins exclusive of lactoferrin.

It is a further object of the present invention to provide preparations for tyrosinase inhibition comprising enzymatic hydrolyzates of milk proteins, exclusive of lactorferrin.

SUMMARY OF THE INVENTION

In accordance with the present invention, hydrolyzates of milk proteins exclusive of lactoferrin comprising peptides having activity of tyrosinase inhibition can be used as an agent for tyrosinase inhibition.

DETAILED DESCRIPTION OF THE INVENTION

Any milk proteins, except lactoferrin, sold in the market such as casein, or its fractions (e.g. α-casein, β-casein and κ-casein), and whey protein or its fractions (e.g. α-lactalbumin, β-lactoglobulin), and a mixture thereof (hereinafter they are referred to as milk proteins) can be used as the source of the hydrolyzates. As noted above, the activity of tyrosinase inhibition of lactoferrin and its hydrolyzates are known. Therefore, exclusion of lactoferrin included in milk proteins is not necessary, but inclusion of lactoferrin in the milk proteins as the raw material of the present invention is not essential. They are subjected to enzymatic hydrolysis in the form of aqueous solution in a proper concentration, typically 5-20% (by weight. the same applies hereinafter unless otherwise indicated).

The enzymes to be used for the hydrolysis are not limited, for example, commercial proteases such as trypsin, chymotrypsin, subtilisin, papain, pepsin, pancreatin, as well as carboxypeptidase derived from yeasts and peptidases derived from lactic acid bacteria can be used. These enzymes can be used individually or in combination. the preferable combination of enzymes is pancreatin, commercial proteases and peptidases derived from lactic acid bacteria.

In general, the enzymes can be used in a quantity from 0.1-5.0% to the quantity of the protein. The hydrolysis can be carried out at a pH range which is closer to the optimum pH values of the enzymes to be used and at a temperature between 15°-55° C. for 10 minutes -24 hours.

After proper reaction period, and with or without neutralization of the resultant reaction mixture, the enzymes are inactivated by heating, and if necessary, the reaction mixture was cooled, filtered, demineralized, concentrated, and/or dried to obtain the hydrolyzates in a liquid or powdery form.

The decomposition rates of the enzymatic hydrolyzates are expressed by the percentage of whole nitrogen to formol nitrogen which is determined by formol titration method (hereinafter referred to as decomposition rate). Preferable decomposition rate is between 6-50%, more preferably 8-45%, in the view point of the effect of the tyrosinase inhibition, however, when elimination of the antigenicity of the protein or the peptide is required, relatively higher decomposition rate within said range is preferable. Though, typical conditions for the hydrolysis are shown in the above, they can be modified in view of the cost performance. More particularly, a combination of the conditions can be decided taking in consideration of the temperature, time, kinds and quantity of enzymes to be used.

The obtained hydrolyzates comprising a mixture of peptides have different molecular weights, and are extremely stable against heating, oxidation and variation in pH.

The hydrolyzates in the form of liquid or powder can be used as an agent for tyrosinase inhibition as it is, and can be formulated by conventional methods as preparations for tyrosinase inhibition. For example, the hydrolyzates can be added to an inert carrier, emulsifier, suspension medium and the like to prepare preparations for tyrosinase inhibition. Certainly any other ingredients of cosmetics and the like, for example, alcohols, perfumeries and/or drugs inclusive of conventional agents for tyrosinase inhibition can be added to the preparations.

The effective quantity of the hydrolyzates is more than 0.05%, preferably from 0.1% -0.5% with which 50% or more of tyrosinase inhibition rate is achieved.

Now an exemplifying test will be described hereunder.

EXEMPLIFYING TEST

The purpose of this test is to exemplify the activity for tyrosinase inhibition of the enzymatic hydrolyzates of milk proteins of the present invention.

(1) PREPARATION OF SAMPLES

Dissolving commercial casein into city water, a 10% casein solution was prepared. After adjusting the pH of the resultant solution to 7.0 with 2M NaOH solution, the solution was pasteurized by heating at 80° C. for 10 minutes then cooled to 37° C. To a portion of the cooled solution, mixtures of commercial protease, AMANO A (Amano Pharmaceutical Co., Ltd.), and SHOYU-ENZYME containing peptidase (by Tanabe Seiyaku) in different concentrations between 0.1-6% were respectively added, the resultant mixtures were subjected to enzymatic reaction at 37° C. for different times from 5 minutes to 24 hours. The resultant reaction mixtures were respectively heated at 80° C. for 10 minutes for inactivation of the enzymes, then lyophilized to thereby obtain various powdery casein hydrolyzates having different decomposition rates between 4-50%.

(2) EXPERIMENTAL METHOD (2-1) Measurement Of Decomposition Rate

The quantities of formol nitrogen and total nitrogen in the samples were determined by formol titration method and Kjeldahl method, respectively. The decomposition rates (D. rate) were calculated by using following equation:

$$D. \text{ rate } (\%) = 100 \times (\text{formol nitrogen} \div \text{total nitrogen}).$$

(2-2) Measurement of Activity for Tyrosinase Inhibition (2-2-1) Preparation of Substrate Solution A 0.045% (w/v) substrate solution was prepared by dissolving a quantity of L-tyrosine (guaranteed reagent, by Wako Junyaku Kohgyo) into 0.1M phosphate buffer solution.

(2-2-2) Preparation of Enzyme Solution

A 0.1% (w/v) enzyme solution was prepared by dissolving a quantity of tyrosinase derived from mushrooms (by Sigma, 3,000 units/mg) into 0.1M phosphate buffer solution (pH 7.0).

(2-2-3) Preparation of Copper Ion Solution

A 1% (w/v) copper ion solution was prepared by dissolving a quantity of copper sulfate (guaranteed reagent, by Wako Junyaku Kogyo) into purified water.

(2-2-4) Preparation of Sample Solutions

Sample solutions were prepared by dissolving each of the samples previously prepared in (1) supra into 0.1 mM phosphate buffer solution (pH 7.0) in different concentrations, 0.05, 0.1, 0.2, 0.5, 1.0, and 4.0%.

(2-2-5) Enzyme Reaction

The substrate solution previously prepared in (2-2-1), each of the sample solutions prepared in (2-2-4) and the copper ion solution prepared in (2-2-3) all of which were preincubated at 37° C. were mixed in the ratio of 0.9 ml: 1 ml: 0.02 ml. To each of the resultant mixtures, 0.08 ml of the enzyme solution prepared in (2-2-2) which was preincubated at 37° C. was respectively added (respectively 2.0 ml in total), then the resultant mixtures were subjected to enzymatic reaction at 37° C. for 3 minutes. To each of the reaction mixtures, 2 ml of 30% acetic acid solution was added to stop the enzymatic reaction, then absorbancy at 640 nm of the resultant solution were respectively measured by a spectrophotometer. The values are represented by the letter B.

As the control, absorbancy at 640 nm of a corresponding mixture wherein 1 ml of 0.1M phosphate buffer solution was substituted for sample solutions was measured in the same manner. The value is represented by the letter A. When the mixtures were not clear enough for the measurement, the corresponding mixtures in each of which the enzyme solution was substituted with 0.1M phosphate buffer solution were prepared and the absorbancy due to the turbidity were measured by the same procedures. The values are represented by the letter C. Using these values, tyrosinase inhibition rates (%) were calculated by using following equation:

inhibition rate $(\%) = 100 \times [1 - \{(B-C)/A\}]$.

(3) RESULTS

Table 1 shows the corelation between the decomposition rates of the hydrolyzates and the activity for tyrosinase inhibition. The tyrosinase inhibition rate of sample 2 having a 4% decomposition rate was only 10% at a 2% concentration of the hydrolyzates. Sample 3 having a 6% decomposition rate showed a 30% inhibition rate at a 0.1% concentration of the hydrolyzates. The higher inhibition rate was observed as the increase in concentration of the hydrolyzates, and about 80% inhibition rate was achieved at a 0.5% concentration of the hydrolyzates, and a 96% inhibition rate was achieved at a 1% concentration of the hydrolyzates.

Either of the samples 4–10 having the decomposition rate between 8–45% showed about 40% inhibition rate merely at a 0.05% concentration of the samples. The inhibition rate increased as the concentration increased, and about 60% or higher inhibition rates were achieved at a 0.10%, 0.25%, and 0.5% concentration of the samples respectively.

TABLE 1

| Sample No. | D. Rate (%) | Concentration of Samples (%) | | | | | | |
|---|---|---|---|---|---|---|---|---|
| | | 0.025 | 0.05 | 0.1 | 0.25 | 0.5 | 1.0 | 2.0 |
| 1 | 0 | 0 | 0 | 0 | 0 | 0 | 0 | 0 |
| 2 | 4 | — | — | 3 | — | 5 | 4 | 6 |
| 3 | 6 | 8 | 20 | 32 | 54 | 77 | 96 | 100 |
| 4 | 8 | 18 | 20 | 57 | 75 | 100 | — | — |
| 5 | 10 | 18 | 38 | 55 | 77 | 100 | — | — |
| 6 | 15 | 20 | 44 | 60 | 81 | 100 | — | — |
| 7 | 20 | 22 | 43 | 65 | 85 | 100 | — | — |
| 8 | 30 | 20 | 40 | 64 | 84 | 100 | — | — |
| 9 | 40 | 21 | 41 | 64 | 80 | 100 | — | — |
| 10 | 45 | 23 | 39 | 60 | 80 | 100 | — | — |
| 11 | 50 | 12 | 21 | 29 | 59 | 82 | 100 | — |

Note: tyrosinase inhibition rate (%)

Now, typical methods for enzymatic hydrolysis and some examples will be described for the better understanding of the present invention. Note that all the materials other than casein and high purity whey protein were sold and readily available in the market. Even if the whey protein contained lactoferrin, the content thereof was negligibly low.

TYPICAL METHOD 1

To 2000 ml of purified water, 300 g of commercial casein was suspended, then the pH of the suspension was adjusted to 8.0 with 1M sodium hydroxide solution to dissolve it completely. After the solution was pasteurized at 80° C. for 10 minutes, the solution was cooled to 40° C., and 15 g of PANCREATIN F (by Amano Pharmaceutical Co., Ltd.) was added and the mixture was kept at 40° C. for 5 hours for enzymatic reaction. The reaction solution was heated at 80° C. for 10 minutes for inactivation of the enzyme, then lyophylized to thereby obtain about 280 g of casein hydrolyzates. The decomposition rate of the resultant hydrolyzates was 21% as measured by the same method as in the Exemplifying Test supra.

TYPICAL METHOD 2

To 2000 ml of purified water, 200 g of commercial casein was suspended, then the pH of the suspension was adjusted to 8.0 by 1M sodium hydroxide solution to dissolve it completely. After the solution was pasteurized at 80° C. for 10 minutes, the solution was cooled to 50° C., and 20 g of PANCREATIN F (by Amano Pharmaceutical Co., Ltd.) and 20 g of AMANO A (by Amano Pharmaceutical Co., Ltd.) and 5 g of SAVORASE (by Imperial Biotechnology Ltd., peptidase derived from lactic acid bacteria) were added thereto, and the resultant mixture was kept at 50° C. for 10 hours for enzymatic reaction. The reaction solution was heated at 80° C. for 10 minutes for inactivation of the enzyme, then lyophylized to thereby obtain about 180 g of casein hydrolyzates. The decomposition rate of the resultant hydrolyzates was 40% as measured by the same method as in the Exemplifying Test supra.

TYPICAL METHOD 3

To 1800 ml of purified water, 120 g of highly purified commercial whey protein, BYPRO (trademark, by Bioisolate, United Kingdom, purity greater than 95%) was dissolved. The pH of the resultant solution was adjusted to 7.0 by 1M sodium hydroxide solution. The resultant solution was pasteurized at 60° C. for 10 minutes and cooled to 45° C., then 20 g of AMANO A (by Amano Pharmaceutical Co., Ltd.) was further added. The resultant mixture was kept at 45° C. for 2 hours for hydrolysis. The hydrolyzed solution was heated at 80° C. for 10 minutes for inactivation of the enzymes, then lyophylized thereby about 110 g of the whey protein hydrolyzates was obtained. The decomposition rate of the hydrolyzates was 15% as measured by the same method as in the Exemplifying Test supra.

TYPICAL METHOD 4

To 200 ml of purified water, 20 g of commercial β-lactoglobin (by Sigma, U.S.A.) was dissolved, the pH of the resultant solution was adjusted to 8.0 by a 1M sodium hydroxide solution. After pasteurization at 60° C. for 10 minutes, the solution was cooled to 40° C. One gram of PANCREATIN F (by Amano Pharmaceutical Co., Ltd.) was added to the solution, then the resultant mixture was subjected to enzymatic hydrolysis at 40° C. for 1 hour. After inactivation of the enzyme by heating the hydrolyzed solution at 80° C. for 10 minutes, the solution was lyophilized to thereby obtain about 180 g of β-lactoglobulin hydrolyzates. The decomposition rate of the hydrolyzates was 10% as measured by the same method as in the Exemplifying Test supra.

EXAMPLE 1

Using 100 g of the casein hydrolyzates prepared in Typical Method 1, about 1000 g of a preparation for tyrosinase inhibition usable for keeping freshness of food was prepared with the following ingredients:

| | |
|---|---|
| casein hydrolyzates | 10% |
| glycine | 80 |
| lysozyme | 10 |

A 20% aqueous solution of the obtained preparation was subjected to tyrosinase inhibition test. The tyrosinase inhibition rate of the solution was 96% by the same method as in the Exemplifying Test supra.

EXAMPLE 2

Using 50 g of the casein hydrolyzates prepared in Typical Method 1, about 1000 g of a preparation for tyrosinase inhibition usable for whitening of the skin was prepared with the following ingredients:

| | |
|---|---|
| casein hydrolyzates | 5.0% |
| sodium hyalronate | 0.1 |
| glyserol | 1.0 |
| purified water | 93.9 |

The tyrosinase inhibition rate of the preparation tested by the same method as in the Exemplifying Test supra was 98%.

EXAMPLE 3

Using 60 g of the casein hydrolyzates prepared in Typical Method 2, about 2000 g of a preparation for tyrosinase inhibition usable for whitening of the skin was prepared with the following ingredients:

| | |
|---|---|
| casein hydrolyzates | 3.0% |
| propylene glycol | 10.0 |
| oreil alcohol | 0.1 |
| ethyl alcohol | 5.0 |
| purified water | 81.9 |

The tyrosinase inhibition rate of the preparation tested by the same method as in the Exemplifying Test supra was 97%.

EXAMPLE 4

Using 40 g of the whey protein hydrolyzates prepared in Typical Method 3, about 2000 g of a preparation for tyrosinase inhibition usable for whitening of the skin was prepared with the following ingredients:

| | |
|---|---|
| whey protein hydrolyzates | 2.0% |
| propylene glycol | 10.0 |
| oreyl alcohol | 0.1 |
| ethyl alcohol | 5.0 |
| purified water | 82.9 |

The tyrosinase inhibition rate of the preparation was 91% as measured by the same method in the Exemplifying Test supra.

EXAMPLE 5

Using 15 g of the β-lactoglobulin hydrolyzates prepared in Typical Method 4, about 1000 g of a preparation for tyrosinase inhibition usable for whitening of the skin was prepared with the following ingredients:

| | |
|---|---|
| β-lactoglobulin hydrolyzates | 1.5% |
| sodium hyarlonate | 0.1 |
| glycerol | 3.0 |
| purified water | 95.4 |

The tyrosinase inhibition rate of the preparation was 98% as measured by the same method in the Exemplifying Test supra.

EFFECTS OF THE INVENTION

The effects of the present invention are as follows:

1) The agent and preparations for tyrosinase inhibition of the present invention are safer than conventional ones, since it derived from naturally occuring milk proteins.

2) The enzymatic hydrolyzates of milk proteins of the present invention are stable to heating and oxidation, and may keep the activity of tyrosinase inhibition for a long period of time.

3) The agent for tyrosinase inhibition of the present invention can be provided in either of liquid or solid form, thus it has wide applications.

What is claimed is:

1. A method for inhibiting tyrosinase activity comprising treating skin with an effective amount of an enzymatic hydrolyzate of milk protein having a decomposition rate of from 6 to 50% by weight as expressed by the percentage of formol nitrogen to total nitrogen, wherein said effective amount is sufficient to result in said hydrolyzate being present in a concentration of 0.05 to 0.5% by weight.

2. The method of claim 1, wherein said decomposition rate is 8-45% by weight as expressed by the percentage of formol nitrogen to total nitrogen.

3. The method of claim 1, wherein said enzymatic hydrolyzate is prepared by hydrolyzing milk protein selected from the group consisting of casein, whey protein, and a mixture thereof with a protease to obtain a hydrolyzate with a decomposition rate from 8 to 45% by weight as expressed by the percentage of formol nitrogen to total nitrogen.

* * * * *